United States Patent [19]

Fleischmann et al.

[11] 4,124,023

[45] Nov. 7, 1978

[54] NON-INVASIVE NUCLEAR DEVICE FOR COMMUNICATING PRESSURE INSIDE A BODY TO THE EXTERIOR THEREOF

[75] Inventors: Lewis Fleischmann, Randallstown, Md.; Glenn A. Meyer, Brookfield, Wis.; Fred Hittman, Baltimore, Md.

[73] Assignee: Hittman Corporation, Columbia, Md.

[21] Appl. No.: 592,718

[22] Filed: Jul. 3, 1975

[51] Int. Cl.² .............................................. A61B 5/00
[52] U.S. Cl. ................................ 128/2 A; 73/708; 73/729; 128/2.05 D; 128/2.05 E; 250/336
[58] Field of Search .................. 128/2 A, 2 R, 2.05 D, 128/2.05 E, 350 R, 350 V, 1 R; 73/393, 406, 407, 418, 409–412; 250/336 R

[56] References Cited

U.S. PATENT DOCUMENTS

| | | | |
|---|---|---|---|
| RE. 26,335 | 1/1968 | Chope | 73/398 |
| 3,034,356 | 5/1962 | Bieganski et al. | 128/2.05 E |
| 3,187,181 | 6/1965 | Keller | 250/360 |
| 3,503,402 | 3/1970 | Schulte | 128/350 V |
| 3,625,199 | 12/1971 | Summers | 128/2.05 E |
| 3,686,958 | 8/1972 | Porter et al. | 73/406 |
| 3,757,770 | 9/1973 | Brayshaw et al. | 128/2 R |
| 3,789,667 | 2/1974 | Porter et al. | 73/406 |
| 4,027,661 | 6/1977 | Lyon et al. | 128/2 A |

OTHER PUBLICATIONS

Bustard; T. S. et al., *IEEE Trans. on Nucl. Science*, vol. 21, No. 1, Feb., 1974, pp. 697–701.

*Primary Examiner*—Kyle L. Howell
*Attorney, Agent, or Firm*—Fleit & Jacobson

[57] ABSTRACT

A non-invasive nuclear device for communicating pressure inside a body to the exterior, such as from within the cranium, bladder or vena cava, of an animal or human, the device including a housing having an interior communicating through a conduit of deformable metallic material with a fluid pressure sensing device positioned within the body portion being monitored, the housing being mounted on the body adjacent the body portion being monitored, a shaped mass of radioactive material together with radiation shield means being disposed within the housing interior together with urging means for producing a predetermined shielding relationship between the radioactive mass and the shield means, the radioactive mass being supported on the urging means for guide movement relative to the shield means and the sensed pressure being exerted through a pressure transmitting fluid flowing within the deformable metal conduit against the urging means for modifying the shielding relationship between the radioactive mass and the shield means proportionally with a change in fluid pressure in the body cavity thereby producing a radioactive output from the radioactive mass corresponding to the magnitude of the fluid pressure in the body position being monitored together with an ambient pressure sensing device mounted on the housing for applying ambient pressure through a pressure transmitting fluid to the urging means in opposition to the sensed body cavity pressure to compensate for changes in ambient pressure.

24 Claims, 7 Drawing Figures.

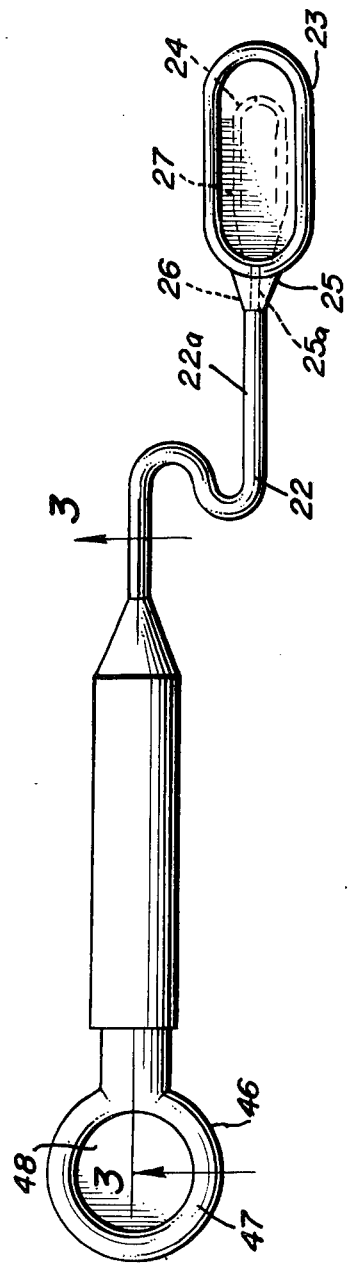
FIG. 2
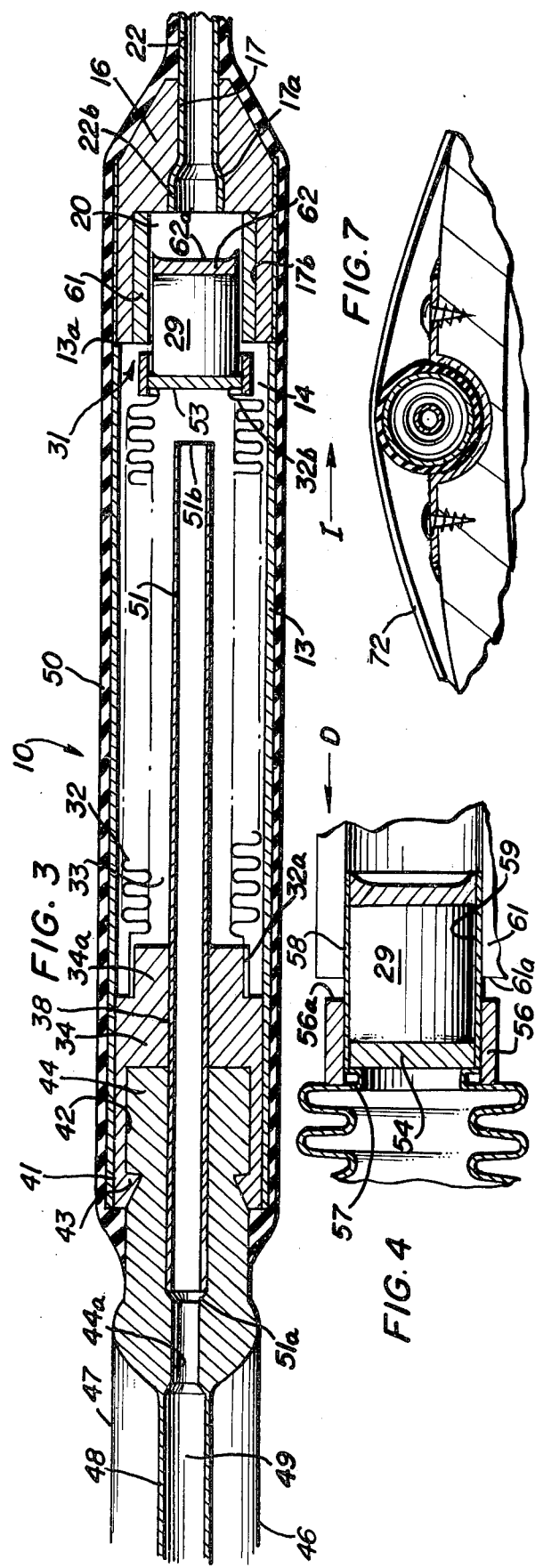
FIG. 3
FIG. 7
FIG. 4

NON-INVASIVE NUCLEAR DEVICE FOR COMMUNICATING PRESSURE INSIDE A BODY TO THE EXTERIOR THEREOF

CROSS-REFERENCE TO RELATED APPLICATION

This invention is related to commonly assigned application Ser. No. 488,988, filed July 16, 1974, for PRESSURE SENSOR, by Warren C. Lyon et al., now U.S. Pat. No. 4,027,661.

BACKGROUND OF THE INVENTION

The need for a non-invasive technique for measuring the pressure in body cavities of animals or humans is recognized as highly desirable for continuous or intermittant monitoring of body conditions. Such cavities as the cranium, vena cava, bladder and others provide valuable and sometimes critical information for maintaining the well-being or survival of an animal or human. For example, it is known that the intracranial pressure provides a valuable indication of well-being for a variety of clinical conditions, including shock trauma and hydrocephalus.

Present-day pressure sensors are intended for permanent implantation for non-invasive utilization of their pressure sensing function. They do, however, constitute a foreign body whose presence may create physical problems which must be obviated for proper functioning of the sensor and for a minimum of discomfort and disfigurement to the patent. For instance, it is highly desirable that the component parts of the sensor external to the body portion being monitored be firmly and securely mounted as any movement of such component parts, particularly when mounted subcutaneously can produce irritation and attendant discomfort to the patient. It is not uncommon for body tissue such as that produced by surgical scars during implantation or muscular growth to interfere with the proper operation of the sensor by imposing pressures on those parts of the device which are designed to be responsive to pressures such as ambient pressure. When such a sensor is used particularly for pressure sensing of the intracranial cavity, the pressure transmitting fluid conduit communicating with the pressure sensing device in the cavity can easily impose pressure on the brain, the sensitive tissue of which can be easily damaged. Furthermore, since such pressure sensing apparatus should be devoid of deterioration during its useful life, which may be for a period of many years, it is highly desirable that the component parts by completely compatible and/or inert chemically and physically with the adjacent body portions so as to avoid any adverse reactions. Additionally, the component parts of the apparatus and pressure transmitting fluid which are in contact should be completely compatible so as to avoid any deteriorating reaction therebetween. In addition, leakage between the component parts is to be avoided, but should there be a failure, the fluid should be compatible in the event of leakage. Furthermore, the parts should remain in perfect working order throughout the useful life of the apparatus. Since such a pressure sensor uses radioactive material, such radioactive material should be of the type which requires no replacement during the useful life of the sensor and it should function in a manner which is non-injurious to the body and to provide a radioactive output in a highly accurate and uniform manner so as to reflect with extreme precision, the sensed body fluid pressure throughout its range of operation under both positive and negative fluid pressures.

SUMMARY OF THE INVENTION

The non-invasive nuclear device of the present invention is fully implantable and is fully capable of communicating pressure inside a body to the exterior thereof to allow read out non-invasively. In its preferred form, the invention includes a housing for subcutaneous implantation with the radioactive source contained in the housing interior and appropriate radiation shield means disposed about the radioactive source.

Urging means such as a bellows are provided in the housing interior which yieldingly urge the radioactive source and shield means into a predetermined shielding relationship, the fluid pressure from a fluid pressure sensing device inserted in the body portion being monitored being transmitted to the housing interior by means of a pressure transmitting fluid through a conduit to move said radioactive source against the force of the urging means out of the initial or repose shielded relationship with the shield means proportionally with an increase in pressure in the body portion being monitored to produce a radioactive output from the radioactive source corresponding to the magnitude of the pressure in the body portion. In one embodiment, the housing is securely mounted on a supporting portion of the body such as a bony structure for permanent implantation under the skin, the mounting means serving as a shield for radiation directed towards the body and to confine the radioactive output to a limited external detection area.

When the inventive device is inserted within a body portion, such as the intracranial cavity, the deformable metal tube may be shaped in accordance with the contours of the body portion thereby avoiding any pressure and attendant injury to adjacent body portions such as the brain. To compensate for changes in ambient pressure, an ambient pressure sensor is mounted on the housing, the interior of which is filled with a pressure transmitting fluid for transmitting the sensed change in ambient pressure to the urging means in opposition to the pressure exerted on the urging means. This ambient pressure sensor includes an annular peripheral portion and a recessed center portion to limit the imposition of pressure on the device by scar tissue or muscular contraction and even concentrated loads such as externally applied forces.

The invention also includes a new and novel radioactive composition to produce a highly accurate radioactive output throughout both the useful life and range of operation of the invention thereby accurately reflecting the true pressure conditions within the body portion being monitored, the radioactive output being of a level which is virtually totally non-injurious to the body.

Thus, the pressure monitoring apparatus of the invention may be simply and easily mounted on or within a body in a concealed, non-disfiguring manner and in a permanently installed position throughout the treatment term of the patient producing virtually no injurious effects on the patient yet producing highly accurate body pressure readings throughout its lift and without mechanical deterioration or malfunctioning and with only slight decay of the radioactive output which is easily compensated for thus eliminating the need for replacement and its attendant surgical problems.

BRIEF DESCRIPTION OF THE DRAWINGS

FIG. 2 is a plan view of the apparatus of FIG. 1;

FIG. 3 is a sectional view taken substantially along line 3—3 of FIG. 2 in the direction of the arrows;

FIG. 4 is an enlarged sectional view of a portion of the apparatus of FIG. 3;

FIG. 7 is a sectional view taken substantially along lines 7—7 of FIG. 5 in the direction of the arrows.

DESCRIPTION OF THE PREFERRED EMBODIMENTS

Figure 1:
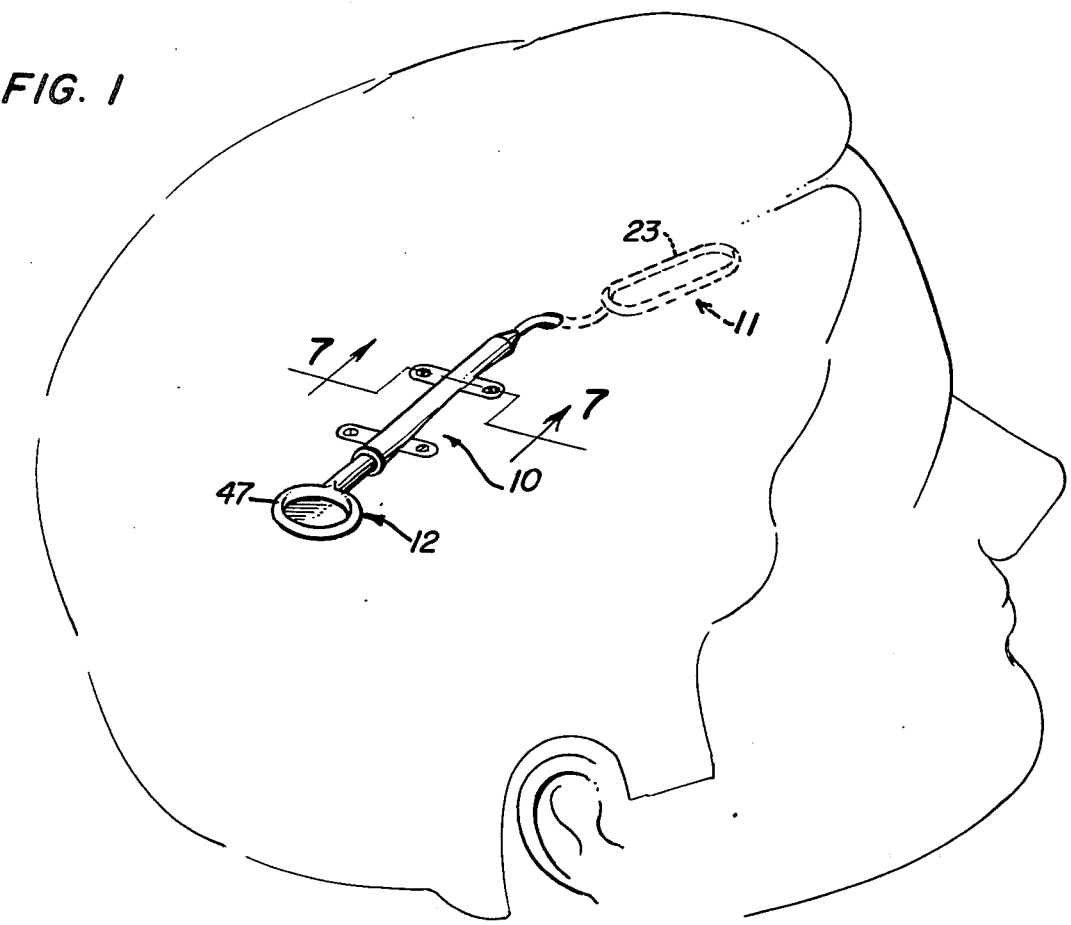
FIG. 1 is a perspective view of a preferred embodiment of the non-invasive nuclear apparatus of the invention in an installed position for monitoring the pressure in an intracranial cavity and communicating the monitored pressure to the exterior of the body.

Referring now to the drawings and to FIGS. 1 and 2 in particular, there is shown the pressure sensing apparatus of the invention with a housing designated generally by the numeral 10, and fluid pressure responsive means designated generally by the numeral 11 and connected to the housing 10 for sensing the fluid pressure in a body portion such as a cavity. Ambient pressure responsive means, designated generally by the numeral 12, is also provided on the housing 10 which is responsive to ambient pressure to compensate for changes in ambient pressure during the operation of the invention. Although the pressure sensing apparatus of the invention is shown in an installed position on the head of a human body for non-invasively monitoring intracranial cavity pressure and communicating it to the exterior, it should be understood that this is only a preferred example of the invention and that it is equally adaptable for monitoring fluid pressure in other areas of the body, both animal and human. Therefore, while the description to follow will be directed to the use of the invention for monitoring intracranial cavity pressure, it should be understood that the invention is equally applicable to monitoring fluid pressure in other body portions and cavities.

Referring now to FIG. 3, and as specifically illustrative of the invention, the housing 10, which is formed of titanium, is preferably of tubular shape having a side wall 13 defining an interior 14. A first support member 16 formed of titanium having a central bore 17 is positioned within one end of the housing 10 in sealing relationship with the housing side wall 13 by means of an epoxy resin or the like. Preferably, an annular shoulder 13a is formed in the housing side wall 13 for positioning the support member 16 in a precise location within the housing 10 as will be explained hereinafter. The first support member central bore 17 is provided with a first portion 17a of slightly enlarged diameter and a second portion 17b of substantially enlarged diameter defining a recess 20 which communicates with the interior 14 of the housing 10.

The fluid pressure responsive means 11 includes a fluid conduit 22 of deformable metallic material preferably titanium which has been heat treated for deformability, one end 22a which is arranged to be connected to a fluid pressure sensing device or tambour 23 having an interior 24 which is arranged to be positioned within a body cavity such as the intracranial cavity of FIG. 1.

The tambour 23 is formed of a suitable elastomeric material such as medical Grade Silastic rubber and is of a substantially flat configuration including a neck portion 25 in the wall of which is molded a helical spring 26 preferably of stainless steel for imparting rigidity to the neck portion 25. The neck portion 25 includes a central bore 25a which communicates with the interior 24 of the tambour 23 and which is arranged to receive the end 22a of the conduit 22 as shown in FIG. 2. Preferably a U-shaped clip 27 of tantulum or the like is disposed within the interior 24 of the tambour 23 for maintaining the side walls of the tambour in spaced-apart relationship and to serve as a locating means for the tambour with the use of x-rays. The tambour or fluid pressure sensing device 23, the fluid conduit 22 and the communicating portions of the housing interior 14, including the recess 20, are filled with a pressure transmitting fluid through which the pressure sensed by the tambour 23 in the body cavity is transmitted to the housing interior 14.

The other end 22b of the conduit 22 is swaged to a suitable enlarged outer diameter so as to conform generally to the inner diameter of the enlarged portion 17a of the first support member central bore 17. The conduit end 22b is pressfitted into the bore portion 17a with the conduit 22 extending through the bore 17 as shown best in FIG. 3. Sealing engagement between the conduit 22 and bore 17 is obtained by means of epoxy resin. Thus, the conduit end 22b communicates with the recess 20 and with the housing interior 14.

A source 29 of radioactive material preferably in the form of a shaped article is disposed within the housing interior 14 together with radiation shield means designated generally by the numeral 31. Means are provided in the housing interior 14 for yieldingly urging into a shielding relationship. More specifically, urging means such as a bellows 32 having an interior 33 is disposed within the housing interior 14, one end 32a of which is mounted on a necked-down portion 34a of a second support member 34 preferably formed of titanium and suitably mounted in the other end of the housing 10 in sealing engagement with the housing side wall 13 by means of an epoxy resin or the like. The other end 32b of the bellows 32 is closed as will be explained hereinafter.

The second support member 34 is provided with a central bore 38 and the necked-down portion 34a is arranged to support the bellows end 32a in a sealing relationship therewith by means of an epoxy resin 41 or the like.

The central bore 38 of the second support member 34 includes a portion of enlarged diameter forming a recess 42 and which is provided with an annular, inwardly directed flange 43. The recess 42 receives the nipple 44 having a central passage 44a of an ambient pressure sensor or tambour 46 forming the ambient pressure responsive means 12. The tambour 46 is formed of a flexible material, preferably an elastomeric material such as medical Grade Silastic rubber, and includes an annular peripheral portion 47 and a recessed central portion 48 defining an interior 49 extending through the nipple central passage 44a.

A suitable adhesive such as a medical Grade Silastic adhesive, seals the nipple 44 in the recess 42 and the annular flange 43 compresses the outer surface of the nipple 44 to form a mechanical compression seal to securely retain the nipple 44 in the recess 42.

A rigid metal tube 51, preferably formed of titanium, is also sealed in nipple 44 and by a Silastic adhesive and extends through nipple central passage 44a and the central bore 38 of the second support member 34 into the bellows interior 33 to communicate the interior 49 of the tambour 46 with the bellows 32. The other end 51b of the tube 51 forms a stop for the bellows end 32b.

In order to transmit the sensed ambient pressure to the interior of the bellows 32, the interior of tambour 46, the bellows interior 33 and the tube 51 are filled with a pressure transmitting fluid, isolated by means of the bellows 32 from the pressure transmitting fluid in the fluid pressure responsive means 11. In the preferred embodiment, all of the exposed metallic surfaces of the sensing apparatus of the invention are coated with a suitable biocompatible material, such as a medical guide Silastic adhesive. As shown in the drawings, this Silastic adhesive 50 extends from the nipple 44 of tambour 46 to the joint between the metal conduit 22 and the neck portion 25 of tambour 23.

In the illustrated embodiment, the radiation shield means 31 includes a first portion 53 of radiation shielding material such as tantalum having a cup-shaped configuration. The first portion 53 preferably includes an end plate 54 preferably in the form of a disc and an annular side member 56 both mounted on the other end 32b of the bellows 32 in closing relationship therewith as shown best in FIG. 4.

The radiation shield means first portion 53 is mounted on an inwardly directed channel portion 57 adjacent the last accordion pleat in the bellows 32, and a tubular sleeve portion 58 extending axially outward therefrom which together define an enclosure 59. The end plate 54 is adhesively secured in the end of the enclosure by a suitable adhesive such as an epoxy resin closing the end 32b of the bellows 32. Similarly, side member 56 is adhesively secured by means of an epoxy resin to sleeve portion 58.

The radiation shield means also includes a second portion 61 in the form of a tubular sleeve of radiation shield material, also preferably tantalum which is press-fitted or the like within the recess 20 of the first support member 16. It can be seen that the second portion 61 extends throughout the depth of the recess 20 and has a forward end edge portion 61a terminating flush with the end of the first support member 16 abutting the housing side wall shoulder 13a. Thus, the second portion end 61a is precisely positioned axially in the housing interior 14 adjacent the end edge portion 56a of the first portion side member 56.

Radioactive source 29 is mounted on the end 32b of the bellows 32 and is slidably accommodated for guiding movement within the radiation shield means second portion 61 disposed in the recess 20. The radioactive source 29 which is preferably of cylindrical shape, having an outer diameter conforming generally to the inner diameter of the bellows sleeve portion 58 is adhesively secured within the enclosure 59 defined by the tubular sleeve portion 58 by means of a suitable adhesive such as an epoxy resin. The end cap 62 having a meniscus 62a is formed by the adhesive material.

The bellows 32 yieldingly urges the radioactive source 29, together with the sleeve portion 58, in the direction of the arrow I into the recess 20 with the edge portion 56a of the radiation shield means first portion side member 56 in adjacent cooperating relationship with the edge portion 61a of the tubular sleeve forming the radiation shield means second portion 61 to establish a shielding relationship with the radioactive source 29. The end cap 62 is therefore disposed oppositely the outlet end 22b of the pressure transmitting fluid conduit 22.

The outer diameter of the bellows sleeve portion 58 is selected to produce a loose-fitting relationship with the inner surface of the sleeve forming the radiation shield means second portion 61 so that fluid introduced into the recess 20 from the end 22b of conduit 22 may flow freely therebetween and through a gap between the front and second portions end edge portions 56a and 61a respectively to fill the interior 14 of the housing 10 on the outside of the bellows 32.

It should be understood that in the assembled apparatus of the invention before installation in a body there is virtually no pressure differential in the housing 10 between the pressure-transmitting fluids on opposite side of the bellows 32. In this condition, there is a gap between the adjacent end edge portions 56a and 61a of the first and second portions 53 and 61 respectively. When the apparatus is installed in the body, the normal fluid pressure in the body cavity slightly increases the pressure on the tambour 23, introducing additional pressure transmitting fluid into the housing interior 14 on the outside of bellows 32, moving the bellows in the direction of the arrow D, thereby increasing slightly the gap between the end edge portions 56a and 61a.

In the operation of the invention after installation, an incease in fluid pressure is sensed in the body cavity by the fluid pressure sensing device or tambour 23, the sensed pressure is transmitted by the pressure-transmitting fluid flowing into the support member recess 20 through the end 22b of conduit 22 around the end cap 62 through the gap between the edge portions 56a, 61a to move the bellows 32 together with the radiation shield means first portion 53 and the radioactive source 29 in the direction indicated by the arrow D in opposition to the urging force exerted by the bellows. During this movement, the radiation shield means first and second portions 53, 61 move apart increasing the gap proportionally with the increase in cavity fluid pressure thereby modifying the shielding relationship between the shield means 32 and radioactive source 29 to expose more of the radioactive source in accordance with the magnitude of the cavity pressure. The radioactive output of the exposed portion of the radioactive source 29 may then be sensed by a conventional nuclear counter or crystal detector disposed externally of the housing 10 and the body.

The provision of the ambient pressure responsive means 12 permits the sensing apparatus of the invention to be responsive to pressure changes in the body cavity regardless of ambient pressure changes. Accordingly, ambient pressure changes are imposed equally on both the ambient pressure responsive means 12 and the cavity pressure responsive means 11 whereby the sensing apparatus of the invention responds to body cavity pressure changes only.

To insure a long life for the sensing apparatus of the invention commensurate with body compatability, it has been found that specific non-reactive fluids and elastomeric materials eliminate such reactions. More specifically, the best results that have been obtained are when the elastomeric material of the various components are formed, in one example, from a Silastic type of silicone rubber and the pressure transmitting fluids are either castor oil or mineral oil between which there is virtually no chemical or physical reaction thereby insuring proper functioning of the invention throughout its life. It has also been found that when the pressure transmitting fluid is a silicone oil, the outstanding results of the invention are accomplished when the materials are selected from the group consisting of butyl, neoprene, Buna N and Viton A rubbers. It should be understood, however, that other elastomeric materials and fluids perform satisfactorily but with less desirable results.

One major concern in selecting a fluid is the osmotic pressure effects produced during implant. It is preferred to eliminate these effects that a simulated cerebrospinal fluid be used as the pressure transmitting medium and it may be used with all materials of construction as it will be compatible with body fluids and will not leak through the elastomeric materials as a consequence of osmotic pressure.

Figure 5:
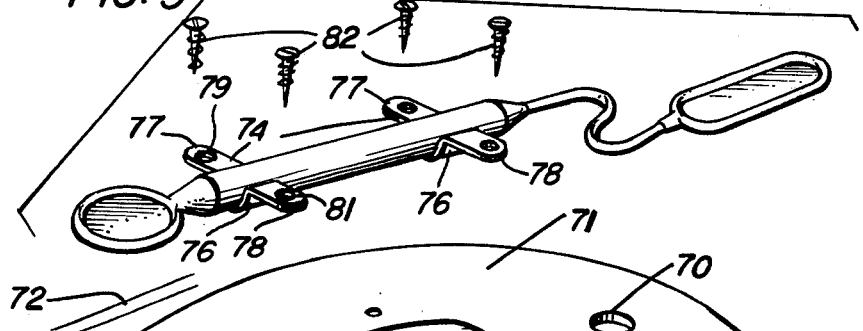
FIG. 5 is an enlarged perspective view of the mounting arrangement for the apparatus of FIG. 1.
Figure 6:
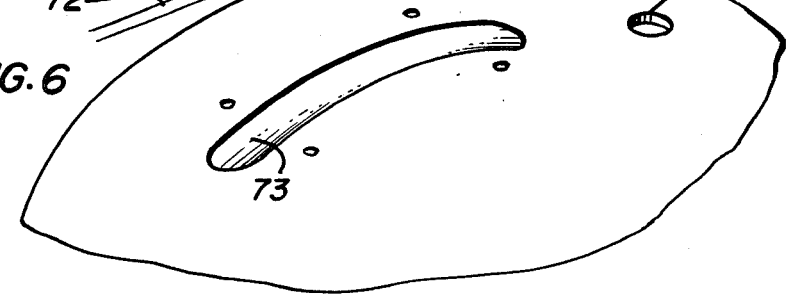
FIG. 6 is a perspective view of a portion of the skull of a patient prior to installation of the apparatus of the invention.

In the use of the invention to monitor the fluid pressure within an intracranial cavity and with reference to FIGS. 5–7, the common practice is to provide a burr hole or aperture 70 within the bony structure of skull 71 overlying the intracranial cavity through which the metallic fluid conduit 22 is inserted, the cavity pressure sensing device 23 being suitably disposed within the intracranial cavity. The housing 10, together with the ambient pressure responsive device 12 are mounted on the outer surface of the skull 71 under the scalp 72.

The apparatus of the invention includes means for permanently mounting the housing 10 and ambient pressure responsive means 12 subcutaneously on the outer surface of the skull 71 in an inconspicuous, securely retained position. More specifically, an elongated concave groove 73 is formed within the outer surface of the skull 71 adjacent the burr hold 70, and mounting means are provided for securing the housing 10 in a seated relationship within the groove 73. The mounting means includes at least one, preferably two, tabs 74 arranged in longitudinally spaced relationship on the housing 10 as shown best in FIG. 5. Each of the tabs 74 includes an intermediate portion 76 of arcuate cross-sectional shape for accommodating the tubular housing 10 in underlying engagement therewith. The tab portion 76 is secured to the outer surface of the housing 10 by suitable means such as a body compatible adhesive, welding or the like. The tabs 74 also include oppositely disposed end portions 77 and 78 extending laterally outward of the housing 10 secured within the intermediate portion 76.

Openings 79, 81 are provided in the tab end portions 77, 78 respectively for accommodating screw means such as screws 82 extending therethrough in threaded engagement with the underlying bone of the skull 71, and with the end portions 77, 78 in overlying engagement with the outer surface of the skull 71, the tab intermediate portion 76 and housing 10 being accommodated within the groove 73.

In the preferred embodiment, the tabs 74 are preferably formed of a radiation shielding material such as tantalum. One of the tabs 74 is positioned on the housing 10 with its intermediate portion 76 extending throughout the path of movement of the radioactive source 61 within the housing. Thus, not only does the one tab 74 prevent downwardly directed radiation into the body, but the radioactive output of source 29 is confined in a non-attenuating manner to the upward directin to permit easy detection by an externally positioned detection device.

The output of the radioactive source 29 need only be of an extremely low order of magnitude typically less than 0.1 microcurie, a magnitude far less than that at which the adjacent body tissue may be adversely affected. However, it should be characterized by an extremely precise and uniform output rate which accurately reflects the changes in fluid pressure within the body cavity throughout its range of operation. The preferred radioisotope used in the present invention is Promethium-145 and to obtain the proper radioactive output from the source 29, it should be in the form of a shaped article of highly homogeneous composition. Accordingly, another novel feature of this invention is provision of such a shaped article of radioactive material.

The radioactive source 29 comprises Promethium chloride ($PmCl_3$) uniformly distributed and absorbed onto an inert carrier such as diatomaceous earth and uniformly distributed throughout a suitable binder such as an epoxy resin. Sources 29 of this composition are extremely uniform regarding the concentration or distribution of the $PmCl_3$.

Although the invention has been described in terms of a single preferred embodiment, nevertheless, changes and modifications will appear evident to those skilled in the art, such as within the purview of the claimed inventive concepts.

What is claimed is:

1. A pressure sensing apparatus for monitoring the fluid pressure in a body cavity comprising, in combination, a housing having an interior, a radioactive source disposed within said housing interior, radiation shield means disposed within said housing interior, means in said housing interior for yieldingly urging said radioactive source and said radiation shield means into a shielding relationship, said radiation shield means including a first portion mounted on said urging means and a second portion supported in said housing interior, said first and second portions of said radiation shield means each partially surrounding said radioactive source, said urging means being arranged to urge said shield means first portion into a cooperating relationship with said shield means second portion for yieldingly maintaining said shield means in said shielding relationship with said radioactive source, fluid pressure responsive means communicating with said housing interior for sensing the fluid pressure in a body cavity, said fluid pressure responsive means being arranged to transmit the fluid pressure in said body cavity to said housing interior for moving said first portion of said radiation shield means relative to said second portion to modify said shielding relationship between said first and second portions incrementally to produce an unshielded radioactive output from said radioactive source corresponding to the magnitude of the fluid pressure in said body cavity.

2. A pressure sensing apparatus in accordance with claim 1 including ambient pressure responsive means communicating with said housing interior for transmitting ambient pressure to said urging means in the direction of the force exerted by said urging means.

3. A pressure sensing apparatus in accordance with claim 1, wherein said fluid pressure responsive means include a fluid pressure sensing device of flexible material for insertion in the body cavity, a fluid conduit for connecting said fluid pressure sensing device to said housing interior and a pressure-transmitting fluid in said fluid pressure sensing device, said fluid conduit and said housing interior for transmitting the fluid pressure in said body cavity sensed by said pressure sensing device to said housing interior.

4. A pressure sensing apparatus in accordance with claim 3, wherein said fluid conduit is formed of deformable material to permit said conduit to be shaped to the contours of the body portions adjacent said body cavity.

5. A pressure sensing apparatus in accordance with claim 3, wherein said fluid pressure sensing device comprises a substantially planar member of flexible material having an interior, said fluid conduit having one end communicating with said housing interior and the other end with the interior of said planar member.

6. A pressure sensing apparatus in accordance with claim 3, wherein said fluid pressure sensing device is formed of a silicone rubber material and wherein said pressure-transmitting fluid is selected from the group consisting of castor oil and mineral oil.

7. A pressure sensing apparatus in accordance with claim 3, wherein said pressure-transmitting fluid is a silicone oil and wherein said fluid pressure sensing device is formed of an elastomeric material selected from the group consisting of butyl rubber, neoprene rubber, butadiene rubber and fluorelastomer.

8. A pressure sensing apparatus in accordance with claim 1, including means for supporting said radioactive source on said urging means.

9. A pressure sensing apparatus in accordance with claim 8, wherein said means for supporting said radioactive source includes said radiation shield means first portion and wherein said second portion of said radiation shield means is arranged to slidably accommodate said radioactive source on said supporting means whereby the radioactive output from said source is proportional to the extent of movement of said first portion of said cooperating relationship with said second portion.

10. A pressure sensing apparatus in accordance with claim 9, including a first support member having a central bore positioned within one end of said housing in sealing relationship with the inner wall of said housing, said first support member central bore having a portion of enlarged diameter defining a recess, and wherein said radiation shield means second portion includes a tubular sleeve of radiation shielding material positioned in said recess for slidably accommodating said radioactive source on said supporting means, means for mounting the other end of said fluid conduit in said central bore in communication with said recess for introducing pressure-transmitting fluid into said recess between said first and second portions and against said urging means in opposition to the force of said urging means, a second support member positioned within the other end of said housing in sealing relationship with the inner wall of said housing and means on said second support member for supporting one end of said urging means in said housing interior.

11. A pressure sensing apparatus in accordance with claim 10, including an ambient pressure sensing device having an interior and formed of flexible material, said ambient pressure sensing device including a nipple having a central passage and wherein said second support member is provided with a central bore, said second member central bore having a portion or enlarged diameter for accommodating said nipple in retained relationship therewith to support said ambient pressure sensing device on said housing, an elongated tube of metallic material extending through said nipple central passage and said second support member central bore for communicating the interior of said ambient pressure sensing device with the interior of said housing and an abmient pressure-transmitting fluid in the interior of said ambient pressure said nipple central passage, said metallic tube and said housing interior and wherein said urging means is arranged to isolate said fluid pressure-transmitting fluid and said ambient pressure-transmitting fluid in said housing interior.

12. A pressure sensing apparatus in accordance with claim 11, wherein said urging means comprises a bellows having an interior and wherein said shield means first portion and said radioactive source are mounted on one end of said bellows, said bellows being mounted on said second support member with its other end in sealing relationship therewith.

13. A pressure sensing apparatus in accordance with claim 12, wherein said supporting means for said radioactive source comprises an end portion of tubular shape having an interior on said bellows one end arranged to be slidably accommodated with said radiation shield means second portion, means for mounting said radiation shield means first portion on one end of said portion of tubular shape for sealing said bellows one end and said one end of said portion of tubular shape, said radioactive source being disposed within the interior of said portion of tubular shape between said radiation shield means first portion and said end cap.

14. A pressure sensing apparatus in accordance with claim 13, wherein said fluid conduit other end is disposed opposite said end cap for introducing said cavity pressure-transmitting fluid into said recess.

15. A pressure sensing apparatus in accordance with claim 14, wherein said radiation shield means first portion includes an end plate and an annular side member disposed adjacent the outer periphery of said end plate for cooperating engagement with said radiation shield means second portion.

16. A pressure sensing device in accordance with claim 3 wherein said flexible material is an elastomer and uses as said pressure transmitting fluid a simulated cerebrospinal fluid.

17. A pressure sensing apparatus in accordance with claim 3, wherein said fluid pressure sensing device is a substantially planar member of flexible material.

18. A pressure sensing apparatus in accordance with claim 1, wherein said body cavity is of the type disposed in underlying relationship with a bony structure and wherein an aperture is provided in said bony structure for accommodating a portion of said fluid pressure responsive means and wherein said housing is adopted to be disposed on the outer surface of said bony structure and including means for securing said housing to the outer surface of said bony structure.

19. A pressure sensing apparatus in accordance with claim 18, wherein said securing means for said housing include at least one clamping member for engaging the outer surface of said housing in retaining relationship therewith and means for attaching said clamping member to the outer surface of said bony structure.

20. A pressure sensing apparatus in accordance with claim 19, wherein an elongated, concave groove is provided within the bony structure outer surface adjacent said aperture and wherein said housing is of circular cross-sectional shape for accommodation with said concave groove and wherein said clamping member comprises a tab having an intermediate portion of arcuate cross-sectional shape for accommodating said housing in underlying clamped engagement therewith and oppositely disposed end portions each having an opening therein and extending laterally outward of said housing disposed within said tab intermediate portion, screw means extending through said openings in said end portions for screw threaded engagement with said bony structure with said tab end portions in overlying engagement with the outer surface of said bony structure and with said tab intermediate portion disposed within said groove.

21. A pressure sensing apparatus in accordance with claim 20, wherein two of said clamping members are provided in longitudinally spaced relationship on said housing and wherein one of said clamping members is disposed on said housing with said arcuate intermediate portion extending longitudinally throughout the length of said radioactive source in said housing in surrounding relationship therewith at least said one clamping member being formed of radiation shielding material.

22. A pressure sensing apparatus in accordance with claim 21, wherein both of said clamping members are formed of tantulum.

23. A pressure sensing apparatus for monitoring the fluid pressure in a body cavity comprising, in combination, a housing having an interior, a radioactive source disposed within said housing interior, radiation shield means disposed within said housing interior, means in said housing interior for yieldingly urging said radioactive source and said radiation shield means into a shielding relationship, said radiation shield means including a first portion mounted on said urging means and a second portion supported in said housing interior, said urging means being arranged to urge said shield means first portion into a cooperating, spaced relationship with said shield means second portion forming a gap therebetween for yieldingly maintaining said shield means in said shielding relationship with said radioactive source, fluid pressure responsive means communicating with said housing interior for sensing the fluid pressure in a body cavity, said fluid pressure responsive means being arranged to transmit the fluid pressure in said body cavity to said housing interior for moving said first portion of said radiation shield means relative to said second portion to modify said spaced relationship between said first and second portions incrementally to produce an unshielded radioactive output from said radioactive source corresponding to the magnitude of the fluid pressure in said body cavity.

24. A pressure sensing apparatus for monitoring the fluid pressure in a body cavity comprising, in combination, a housing having an interior, a radioactive source disposed within said housing interior, radiation shield means disposed within said housing interior, means in said housing interior for yieldingly urging said radioactive source and said radiation shield means into a shielding relationship, said radiation shield means including a first portion mounted on said urging means and a second portion supported in said housing interior, means for supporting said radioactive source on said urging means, said radiation shield means second portion being arranged to slidably accommodate said radioactive source on said supporting means in loose fittng relationship therewith to define a flow passage therebetween, said urging means being arranged to urge said shield means first portion into a cooperating relationship with said shield means second portion and to urge said radioactive source within said shield means second portion, fluid pressure responsive means communicating with said housing interior for sensing the fluid pressure in a body cavity, said fluid pressure responsive means being arranged to transmit the fluid pressure in said body cavity to said housing interior through said flow passage for varying said cooperating relationship between said first and second portions and the position of said radioactive source in said second portion to modify said shielding relationship by exposing said radioactive source with infinite resolution to produce an unshielded radioactive output from radioactive source corresponding to the magnitude of the fluid pressure in said body cavity.

* * * * *